(12) United States Patent
Braeuning et al.

(10) Patent No.: US 6,595,641 B1
(45) Date of Patent: Jul. 22, 2003

(54) DEVICE FOR EXAMINING OCULAR MOTILITY

(75) Inventors: Johannes Braeuning, Ostfildern (DE);
Gerhard Braeuning, Ostfildern (DE);
Hans-Juergen Thiel, Tuebingen (DE);
R. Kemp Massengill, Escondido, CA (US)

(73) Assignee: PlusoptiX AG (DE)

( * ) Notice: Subject to any disclaimer, the term of this patent is extended or adjusted under 35 U.S.C. 154(b) by 0 days.

(21) Appl. No.: 09/720,133

(22) PCT Filed: Jun. 22, 1999

(86) PCT No.: PCT/EP99/04322
§ 371 (c)(1),
(2), (4) Date: Feb. 28, 2001

(87) PCT Pub. No.: WO99/66829
PCT Pub. Date: Dec. 29, 1999

(30) Foreign Application Priority Data

| Jun. 23, 1998 | (DE) | ..... 298 11 062 U |
| Sep. 16, 1998 | (DE) | ..... 198 42 394 |
| Sep. 16, 1998 | (DE) | ..... 198 42 393 |
| Nov. 5, 1998 | (DE) | ..... 198 50 897 |

(51) Int. Cl.$^7$ ................................................. A61B 3/14
(52) U.S. Cl. ..................................... 351/208; 351/209
(58) Field of Search ............................... 351/237, 238, 351/239, 242, 240, 243, 201, 202, 208, 209, 210, 211, 246

(56) References Cited

U.S. PATENT DOCUMENTS

| 5,042,937 A | 8/1991 | Cornsweet | ............... 351/204 |
| 5,309,185 A | 5/1994 | Harper | ............... 351/202 |
| 5,530,492 A | 6/1996 | Ron | ............... 351/201 |
| 5,852,489 A | * 12/1998 | Chen | ............... 351/237 |

FOREIGN PATENT DOCUMENTS

| DE | 40 41 332 | 7/1992 |
| EP | 0 830 839 | 3/1998 |
| WO | WO 96/00031 | 1/1996 |
| WO | WO 96/13195 | 5/1996 |

OTHER PUBLICATIONS

Cheung et al., "Strabismus Examination by Telemedicine", Ophthamology, vol. 107, No. 11, Nov. 2000, pp. 1999–2005.

* cited by examiner

*Primary Examiner*—George Manuel
(74) *Attorney, Agent, or Firm*—Crowell & Moring LLP

(57) ABSTRACT

A device for examining ocular motility of an individual includes a display surface for displaying a fixation light thereon, an arrangement for determining the position of the individual's head, and/or an indicator that can be adjusted with respect to position on the side of the individual to indicate the indicator points, representing his or her subjective visual impression, on the display surface. A position sensor is provided for adjustment and/or detection of the orientation and distance of the individual's head in relation to the display surface; and a sensor mechanism detects and determines the position of the indicator point on the display surface. Data about the position of the individual's head in relation to the display surface and about the position of the indicator point on the display surface are transmitted to an evaluation unit, which processes this information to determine at least one ocular motility characteristic of the individual.

17 Claims, 6 Drawing Sheets

DEVICE FOR EXAMINING OCULAR MOTILITY

BACKGROUND AND SUMMARY OF THE INVENTION

This application claims the priority of German patent documents 298 11 062.8, filed Jun. 23, 1998; 198 50 897.2, filed Nov. 5, 1998; 198 42 393.4, filed Sep. 16, 1998; and 198 42 394.2, filed Sep. 16, 1998 and PCT International Application No. PCT/EP99/04322, filed Jun. 22, 1999, the disclosures of which are expressly incorporated by reference herein.

The invention relates to a device for examining ocular motility.

In conventional examination techniques for detecting ocular motility disturbances (respectively, genuine or latent strabismus), the person being examined ("test person") looks simultaneously with both eyes at a white, point-shaped spot of light. At the same time a (dark) red glass is placed in front of one eye. As the so-called guide eye, this eye perceives then only the white light as a red spot of light, without surroundings. The other eye perceives the white light and the surroundings as a double image. In this manner the visual impressions of both eyes are separated.

If both eyes are not aligned correspondingly parallel, or of the light is not imaged on the corresponding retinal areas, the test person perceives subjectively the white spot of light as deviating from the red spot of light. To measure the horizontal and vertical distance between the spots of light, a display screen with a grid graduation (e.g., a so-called Harms tangent scale), is used. The center of the display screen exhibits a point-shaped white light source for the purpose of making a point-shaped spot of light available. The test person points with an optical pointer to the place on the display screen, where he perceives subjectively the red spot of light. In this manner the examining personnel can then read from the display screen the distance between the indicator's spot of light and the central spot of fixation light and from this information derive quantitatively, e.g., the angle of squint and qualitatively with respect to convergence, divergence, or vertical difference.

In order to conduct the examination for different lines of sight, the test person normally wears a forehead lamp, which projects an indicating light on the tangent scale. The perception of double images for different lines of sight can be tested only if the head of the test person is tilted in different directions and the test person looks steadily at the central fixation light of the tangent scale. The tilt of the head is then determined by reading the indicating light on the tangent scale. If, instead of a point-shaped source of fixation light, a linear source of fixation light that can be rotated, for example, by means of a stepping motor, is used, then this examination method can be used to measure the rotational differences between both eyes. To this end, the test person receives a controller for rotating the linear source of fixation light and aligns the red and white lines of light that he perceives.

The customary examination method that is explained above is relatively space intensive, since a typically 3 m×3 m tangent scale is used. Furthermore, it is also labor intensive, since examining personnel are required to read and interpret the various data from the tangent scale.

Published International patent application WO 96/13195 A1 describes a process and a device of this class for determining horizontal, vertical and/or cyclo-deviations of the eye of a test person. It also provides a device for generating an essentially point-shaped and/or linear fixation light on a board, arranged in the test person's field of vision. The fixation light is imaged by an optical system as a virtual object point or a virtual object line at predetermined positions on the board. Furthermore, there are means to hold the head of the test person in a fixed position relative to the distance and orientation of the board. To indicate the subjective visual impression, a pointer that can be operated by the test person serves as a part of the optical projection system, which images an indicator light as a virtual object point on the board. The degree to which the test person adjusts the pointer to indicate the subjective visual impression can be measured with sensors and displayed optically and/or fed to a microprocessor.

One object of the invention is to provide a device of the type described above which can be used to examine one or several ocular motility parameter(s), with savings in space, time and personnel.

This and other objects and advantages are achieved by the ocular motility evaluation device according to the invention, which includes position sensors for adjustment and/or detection of the orientation and distance of the head of the test person in relation to the display surface and/or a sensor mechanism for detecting and determining the indicator points, representing the test person's subjective visual impression, on the display surface. In addition, there are computerized evaluation means, to which are transmitted data about the position of the test person's head with respect to the display surface and about the position of the indicator point on the display surface. These evaluation means evaluate this information in order to determine at least one ocular motility characteristic, such as squint angle.

As a consequence, this device significantly automates the motility examination, compared to the conventional procedure explained above. The computerized evaluation means relieve the examining individual of the corresponding evaluating tasks. The presence of the position sensor mechanism for adjustment and/or detection of the orientation and distance of the test person's head in relation to the display surface simplifies adjustment of the test person's head for the examining personnel; or it is possible to leave the test person's head unfixed, detect its position with sensors and consider this information correspondingly in the evaluation means. With the presence of a sensor mechanism for determining the position of the indicator point, there is no need for the examining personnel to read the point from the display surface, to which the test person is pointing. Rather this is done automatically by the system. The device, according to the invention can use a tangent scale which is significantly smaller than the conventional dimensions, or a comparably, grid-structured display screen or also a simpler, unstructured display surface, like a simple wall.

In one embodiment of the invention, the display surface is approach sensitive (e.g., touch sensitive). For this purpose, a current so-called digitizing board can be used, for example. Then the test person can mark (with, for example, a finger or a pointer) the indicator point corresponding to his subjective visual impression, on the display surface, whose proximity sensor mechanism records this indicator information and transmits it as high resolution information about the indicator point to the computerized evaluation means. The need for reading the indicator point by the examining personnel is thus dispensed with.

Another embodiment of the invention includes a photosensitive display surface. For the display of his subjective visual impression there is for the test person a light pointer for generating a correspondingly point-shaped spot of light or a spot of light exhibiting another structure. Then the photosensor means of the display surface detects the place to which the test person aims the spot of light in accordance with his subjective visual impression, and transmits the corresponding high resolution data about the indicator point to the computerized evaluation means.

According to another feature of the invention, the indicator means may contain a mobile pointer, which can be operated by the test person. A pointer-position sensor mechanism shows the exact position (i.e., the position and orientation) of the pointer in three dimensional space as a measure for the indicator point on the display surface, to which the test person points with the pointer. In this manner the information about the indicator point can be obtained automatically from the system, without need for corresponding sensor means at the display surface.

According to still a further feature of the invention, a headlight projection unit can be fixed to the head of the test person for determining the position of the test person's head. The headlight projection unit projects one or more spot(s) of light that indicate(s) the position of the head on a photosensitive display surface. Then its photosensor means determine the exact location of the spot of light on the display surface, indicating the position of the head, on the display surface and transmit the corresponding data on the position of the head to the computerized evaluation means. In this manner permanent fixing of the test person's head can be dispensed with.

The latter is also possible with the device, according to another embodiment of the invention, which comprises a tracking system that is worn on the test person's head and detects its position in three dimensional space. From this information then in the prior art arrangement of the display surface the orientation and the distance of the test person's head can be determined automatically. Thus, with this device the position of the test person's head can remain totally or partially unfixed, and can be detected by the system without the sensor mechanism on the side of the display surface.

In a further embodiment, the means for determining the position of the test person's head contain an optical or ultrasound distance measuring device, with which the system automatically determines the distance and optionally also the lateral position of the test person's head from the display surface.

Still another embodiment of the invention, includes a video camera system with related image evaluator, which finds the position of the test person's head in space, the position of a test person-operated pointer in space, the position of a spot of indicator light, representing the subjective visual impression of the test person, and/or the position of a spot of light, which indicates the position of the head and is produced by a headlight projection unit, on the display surface.

Finally, in yet another embodiment, the computerized evaluation means contain a neural network or an expert system, known to the expert, whereby they are designed primarily for diagnostic evaluation with respect to one or several eye motility parameter(s). It is possible for the expert to implement these evaluation means by using the evaluation algorithms, which are known per se for this diagnostic purpose and which he can implement in the neural network or expert system under discussion.

Other objects, advantages and novel features of the present invention will become apparent from the following detailed description of the invention when considered in conjunction with the accompanying drawings.

DETAILED DESCRIPTION OF THE DRAWINGS

Figure 1:
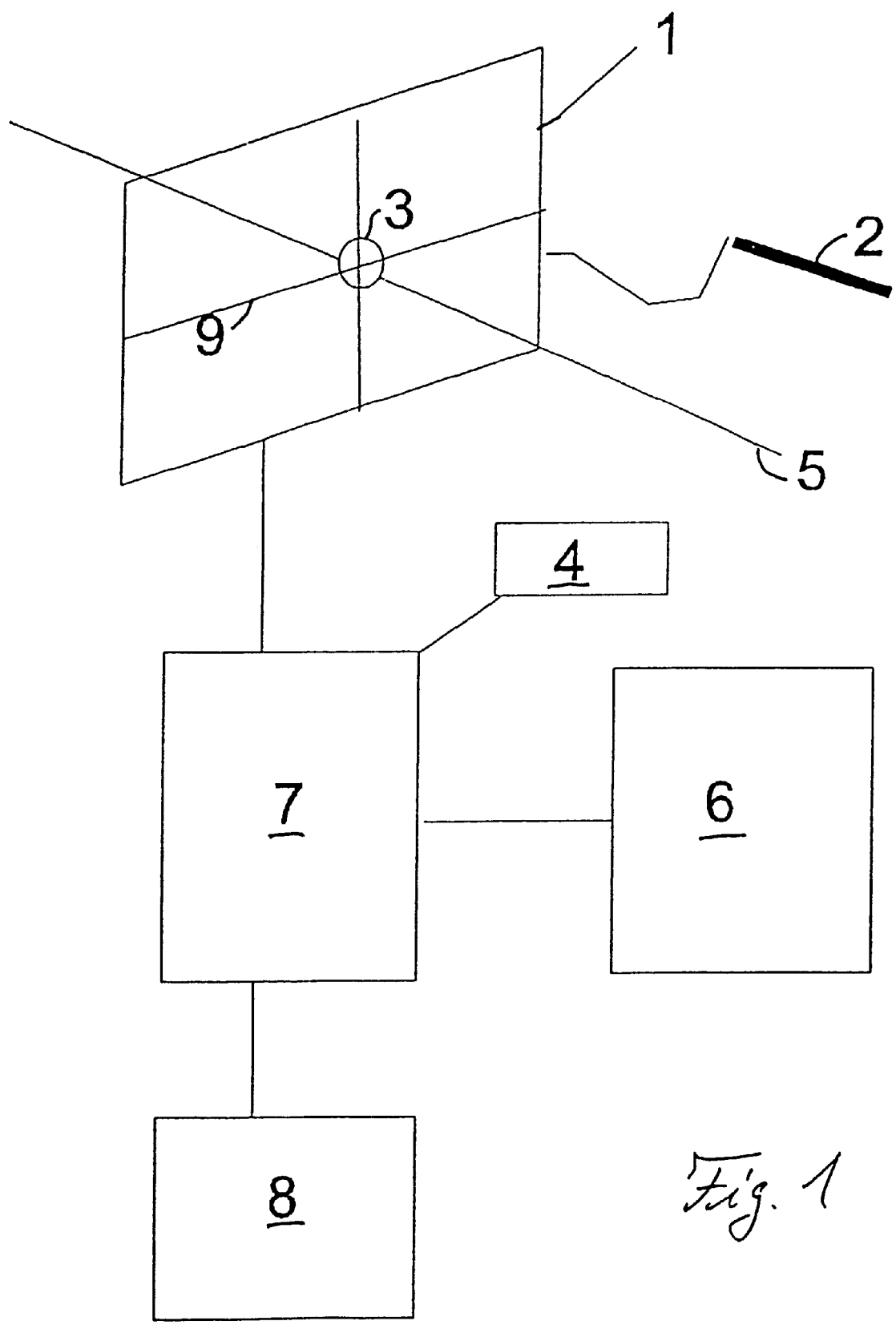
FIG. 1 is a schematic block diagram of a device according to the invention for examining the eye motility.

The device, which is depicted as a schematic drawing in FIG. 1 and whose purpose is to examine ocular motility, comprises a display panel 1 equipped with at least one point-shaped, centrally arranged source of fixation light 3 and a grid scale graduation 9. Associated with the display panel 1 is an indicator means 2 that can be operated by a test person to indicate indicator points, representing his subjective visual impression, on the display panel 1. Furthermore, there are means 4 for determining the position and distance of the test person's head in relation to the display panel 1. The resulting data concerning the position of the indicator point on the display panel 1 and the position of the test person's head in relation to the display panel 1 are recorded by an attached evaluating computer 7 and evaluated for diagnostic purposes (e.g., for determining the angle of squint). The examination findings, obtained from the computer 7, and the results of the examination can be shown on a monitor 6. A printer 8 serves to print out the corresponding data.

One examination method with fusion separation consists of the light source 3 (e.g., an LED), which lies in the center (that is, the longitudinal central axis 5 of the display panel 1), radiating a white fixation light, at which the test person looks with one eye through a red glass and with the other eye uncovered. Then the test person perceives this light source 3 as double, owing to the fusion separation. The test person or the examining individual marks the position of the light source, which appears red to him, with the pointer 2 on the display panel 1. Then the system recognizes automatically the position of the indicator or marker spot on the display panel 1; and from this information the computer 7 finds the distance between the indicator point and the fixation light source 3 and from this information the angular deviation between the right and the left eye. This procedure is carried out for different lines of sight.

The position of the marker or indicator spot on the display panel 1, which represents the subjective visual impression of the test person, can be found internally by the system, for example, by means of an approach sensitive (e.g., touch sensitive) display panel. The proximity sensor mechanism can work in the customary manner on a capacitive, electromagnetic, surface acoustical or resistive principle. In particular, for this purpose it can be formed in the conventional manner by a digitizing board, which is provided with the central source of fixation light 3 and optionally with the scale structure 9. Then the test person points with his finger or a pointer to the corresponding point on the digitizing board, whose proximity sensor mechanism recognizes the place of approach or touch and transmits the data about the indicator point to the computer 7.

The different lines of sight can also be detected internally by the system, for example, by using a conventional so-called tracking system as the means 4 for determining the position of the test person's head. The tracking system is worn on the test person's head, and can detect its position in three dimensional space and report to the computer 7. Optionally it is sufficient to report the head's angle of tilt relative to the longitudinal central axis 5 of the display panel 1, when the distance of the test person's head from the display panel 1 is known, or detected elsewhere (e.g., by fixation of the distance, or by an optical or ultrasound distance measuring device provided for this purpose).

Another possibility for setting different lines of sight is to have the test person fix several fixation light sources, which are installed off-centered on the display panel 1, without moving his head.

Another alternative provides that a photosensitive display panel 1 is used; and a headlight projection unit, which produces a spot of light, indicating the position of the head, on the photosensitive display surface 1, is fixed to the test person's head. This spot of light can be recognized in high resolution by the photosensor means of the display panel 1 and reported to the computer 7, which can determine from this information the current tilt of the head. Optionally the examining individual can read the position of the spot of light, indicating the position of the head, from a display panel 1 provided with the scaling 9, and enter it into the computer 7.

As another alternative for the examination, a linear, rather than point-shaped, source of fixation light 3 can be used, e.g., with the aid of a suitable diffuser, to measure and calculate the cyclo-rotation of the eyes. To this end, the test person marks individual points of the double line image, which he perceives.

As another application, the field of binocular single vision can be marked with the pointer 2. In this case the test person does not wear any colored filter in front of an eye, but rather marks the outer boundaries on the display panel 1. Among these boundaries he perceives the fixation light as a single image.

It is clear that the source of fixation light 3 need not necessarily be white; rather it can be any arbitrary color. It can be switched on or off by the computer 7 or with a hand switch. The glasses worn by the test person can contain, in addition to the aforementioned colored filter, one more spherical glasses and/or prisms, depending on as a function of the application. The headlight projection unit can exhibit any arbitrary, desired shape for the spot of light, like a point or a cross, where the light source can be formed, e.g., by a laser. Instead of the aforementioned linear source of fixation light, the cyclo-rotation of the eyes can also be measured by a simultaneous presentation of at least two single points of fixation light. For diagnostic evaluation, the computer 7 can include a conventional expert system or neural network, where the necessary evaluation algorithms, known to those skilled in the art are implemented.

Figure 2:
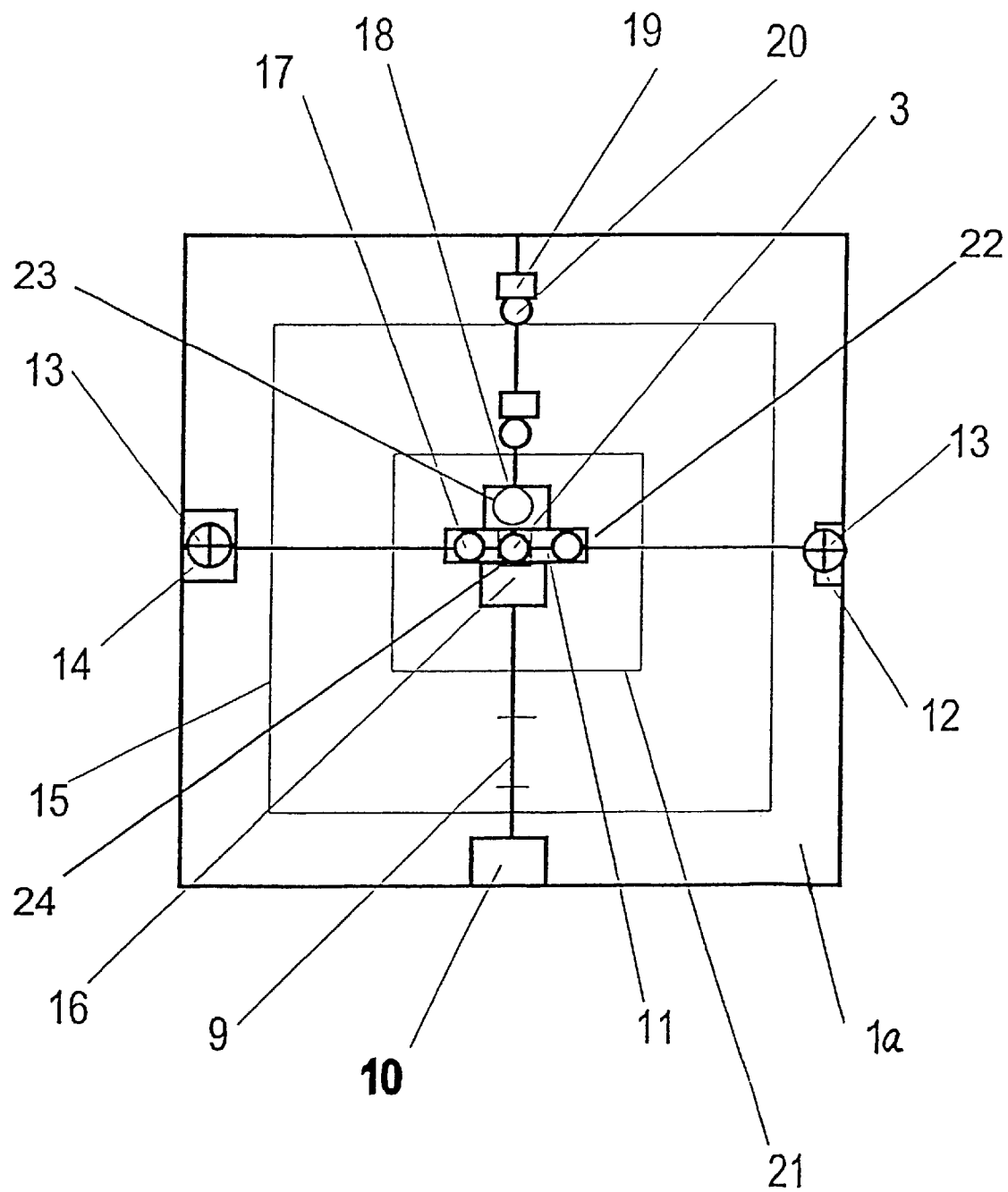
FIG. 2 is a top view of a digitizing board, used in the device of FIG. 1 as the display surface.

FIG. 2 is a more detailed front view of a touch and/or photosensitive digitizing panel 1a which can be used as a display panel 1 in the device of FIG. 1. Attached to the center of this digitizing unit or this digitizing board 1a is the source of fixation light 3, which permits, instead of the point-shaped radiation of light, also the presentation of a linear light source 11, to which end it is assigned a suitable diffusor. As stated, the cyclo-rotation of the eyes can be found with the linear source of fixation light 11. The line of fixation light 11 can also be rotated around the longitudinal central axis of the digitizing board 1a, by means of a stepping motor 22, which can be operated by the computer 7 with an automatic controller or with a hand-operated controller. Thus, the test person can align his double line image. As an alternative, the alignment can comprise the marking of individual points of this line. As an alternative to the use of the linear light source 11, the arrangement of several individual sources of fixation light 17 on a line can be provided. It is clear that the digitizing board 1a of FIG. 2 is also suitable for marking the field of binocular single vision.

To detect automatically the indicator or marker point, at least one specific subarea 15 of the digitizing board 1a is approach and/or photosensitive. In the touch sensitive layout, the related contact sensor mechanism detects the location on the digitizing board 1a that the test person touches with a finger or a pointer or the like. In the photosensitive design the digitizing board 1a is assigned an optical pointer, with which the test person can aim a corresponding spot of light on the place on the digitizing board 1 to be marked. Its photosensor means detect the place of the indicator's spot of light and report it to the evaluating computer 7.

As an alternative, the marker or indicator point can also be detected internally by the system by means of two cameras 10, 14, which are arranged in the center of two adjoining display panel sides with the field of vision parallel to the display panel and thus detect the horizontal and vertical position of a finger or a pointer, etc. To this end, the cameras are assigned a suitable image evaluator, which can be located in the evaluating computer 7. Instead of the cameras 10, 14, infrared transmitters can be positioned there and assigned corresponding infrared sensors 12 on the respective opposite display panel side.

If for the purpose of detecting the position of the head, a headlight projection unit is fixed to the head of the test person, corresponding photoresistors 19 can be provided on the display panel 1a. Said photoresistors detect the direction of the head-worn projection lamp with the aid of the spot of incident light, indicating the position of the head. To determine the distance of the test person from the panel 1a, two light projection systems 13 can be attached at a defined angle of their optical axes to the head of the test person, in particular to the glasses he is supposed to wear or, as an alternative, on the panel 1a. If the spot of light is projected from the test person's head on the panel 1a, the intersecting points of the projected light spots merge at a point at a defined distance of the test person's head from the panel 1a. If light spots are projected from the panel 1a onto the face of the test person, such light spots merge correspondingly in the face of the test person at a defined distance, representing the desired examination distance. When horizontally or vertically projected figures are used, it can be checked whether the test person is holding his head straight. As an alternative, the adjustment or detection of the distance of the test person's head from the panel 1a can be carried out by means of an ultrasound distance measuring unit 16. In so doing, the ultrasound transducer can be fixed on the panel 1a or at the head of the test person.

Preferably the scale, affixed to the digitizing board 1a and exhibiting angular degrees, can be interchanged. Also suitable is the use of a central display screen 21, which makes it possible to detect the marker or indicator points, which reproduce the subjective visual impression of the test person, by way of a cursor controller, e.g., a computer mouse. Another option for determining the marker or indicator point on the panel 1a is to use a video camera system with assigned image evaluator; in this manner it is possible to determine the position of a contact or optical display of the marker point by the test person on the panel 1a, with high resolution.

As an alternative, the tilt angle of the test person's head relative to the display panel 1a can be fixed by attaching to the panel 1a the fixation light source 3 or an additional light source 23, which is recessed in a sleeve 24 of defined length or at a corresponding depth. Thus, it can be seen by the test person only in a defined position of the head.

optionally the position of the test person's head and/or the position of the indicator point, representing the subjective visual impression on the display panel 1 can be determined by means of an assigned, conventional three dimensional tracking system which makes it possible to find at least the tilt of the marker or the head of the test person, and reports to the evaluating computer 7 the corresponding data regarding the horizontal, vertical and rotational tilt. If such a test person head-tracking system is expanded by a distance measurement (for example, using ultrasound or an optical or electromagnetic measurement method), the position of the head in three dimensional space can be detected completely by the system, without having to fix the test person's head.

Another possibility for detecting the position of the test person's head when it is not fixed in position is to attach (as stated) a point-shaped light source to the test person's head and to provide the display panel 1 with a photosensitive surface so that it detects the projected light spot in high resolution. From this information, the tilt of the head can be determined by the evaluating computer 7.

If desired, by providing (for example) optical indicating means on the display panel 1 such an arrangement can also be used to assure that the test person holds his head in a specific, desired examination position. For this purpose he moves his head so that the spot of light projected by his headlight projection unit is coincident with the fixation marker, which is activated on the display panel 1 and which can also be, for example, a screen mouse indicator.

If the pointer 2 is assigned such a three dimensional tracking system, there is no need for the described detection of the touch or photosensitive marker point on the display panel 1. In this case, the marker or indicator point can be found by the evaluating computer 7 indirectly from the data on the position of the tracking system, assigned to the pointer 2.

Figure 3:
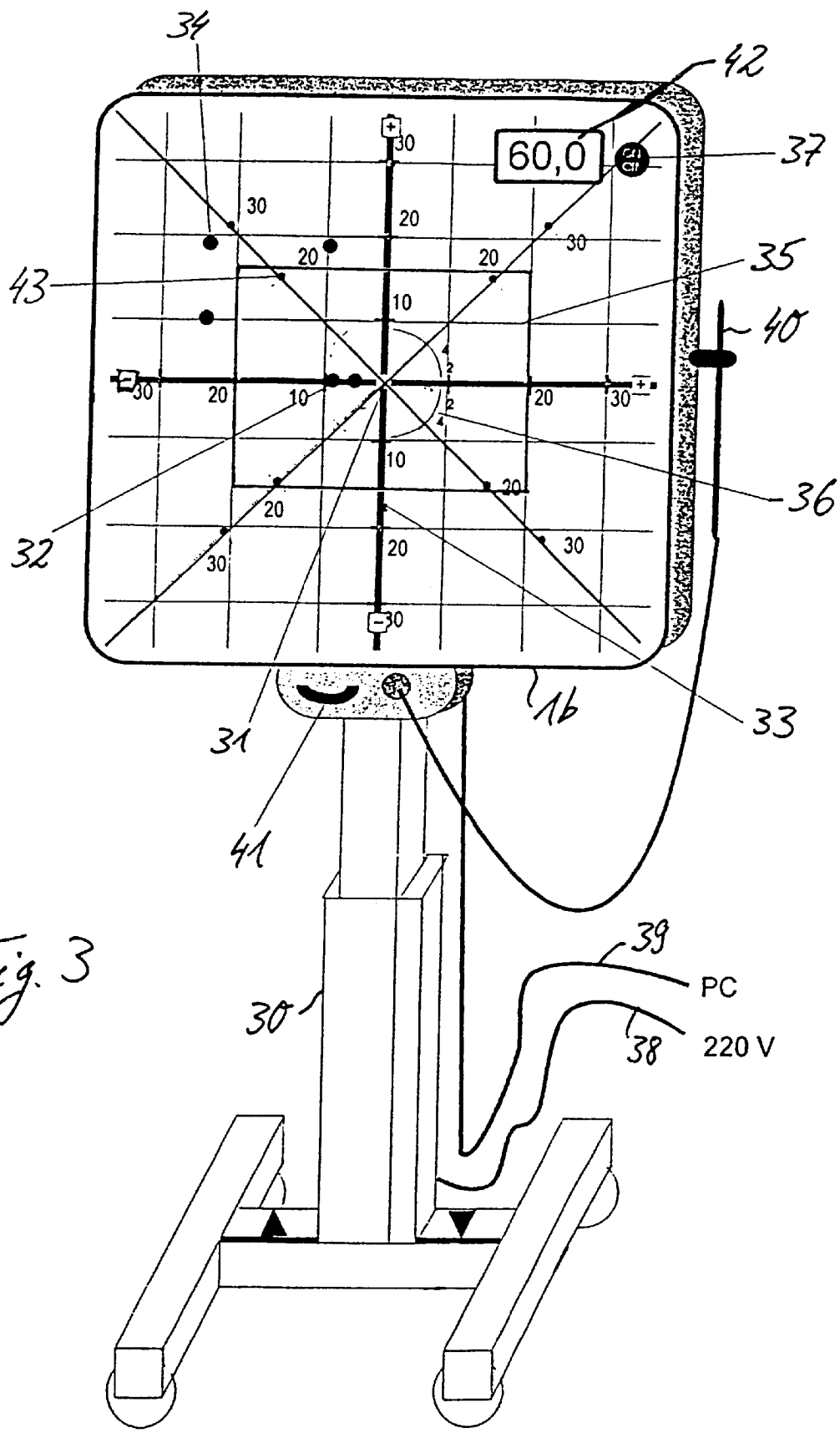
FIG. 3 is a perspective view of another example for a touch sensitive display surface with related peripherals.

FIG. 3 shows a very comfortable and user friendly design of an ocular motility examination device. In this embodiment the display surface is formed preferably by a touch and/or photosensitive display panel 1b, whose functionality is equivalent in essence to the digitizing panel 1a of FIG. 2, and is carried by a vertically adjustable frame 30 that is mounted on rollers. The display panel 1b is provided with a rectangular grid structure. As an alternative, scaling with curved lines can also be used; and a fixation light LED 31 is disposed in the center. Optionally an optical distance measuring unit 32 is attached in the vicinity of the central fixation light 31 on the panel 1b. The main axes 33 of the grid are emphasized with thick lines. Optionally an ultrasound distance measuring unit 34 can be attached to the panel 1b.

The active range of measurement is described by a rectangular frame 35. Inside the active measurement range 35 there is also a circular scale 36 for measuring cyclorotation. In the top right corner area there is an on and off switch 37 in the form of a corresponding contact switch and an LCD display 42, where the current distance between the test person's head and the display screen 1b can be displayed as a numerical value. Optionally it is possible to have a display with a red and a green LED, with which it can then be displayed whether the test person's head is or is not at the correct distance relative to the panel 1b for the examination.

The display panel 1b, designed preferably as a touch sensitive digitizing board, can be provided with the necessary operating voltage by means of a power cable 38 and delivers its various, aforementioned measurement data over a data line 39 to the evaluating computer, formed by, for example, a PC. A pointer 40 with a cord serves as the indicator. As an alternative, a cordless pointer can also be used. A number of other light diodes 43 (for example, sixteen of them), which are distributed over the display surface 1b and which can be activated by the computer, can be used optionally for guiding the vision and tilting the test person's head during the examination.

The entire construction of the digitizing board can be set up in the examination room as desired with the handle 41 and the roller mount. It must be noted that a display panel 1b, whose area is relatively small compared to the conventional tangent scales, Hess screens or Maddox crosses, can be used. Its dimensions are only, for example, 80 cm×80 cm. Furthermore, instead of a sensor equipped display panel, like the illustrated digitizing board 1b, a display surface without sensors can also be used in accordance with the invention. For example, a simple wall of an examination room can be used if the detection of the position of the head and the detection of the marker points can cope without the aid of such a sensor mechanism on the display surface, as in the case of the aforementioned tracking systems for the head posture and the pointer.

It is expedient to assign to the display panel a microcontroller, which digitizes the measurement signals of the various sensors and transmits them to the computer, and also receives the control signals from the computer and converts them for the purpose of activating the various activatable units on the display panel.

Depending on the application and the design of the system, the inventive device can also include in particular the following additional measures and properties.

For the indicator means a pointer can be provided with an attachment (e.g., in the shape of a ring), which can be optionally illuminated. Thus, at the end of the examination, the patient can be put into the position of no longer pointing to a fixation light, but rather "capturing" it with the attachment, e.g., the ring. The patient can frequently better recognize the attachment as, for example, a conically tapering pointer tip, since the ring does not fall into the double image scotoma.

To measure the field of binocular single vision, indicator means (e.g., a point-shaped light source equipped for illumination), can be used. The sensor mechanism for determining the position of the indicator detects the eccentricity, at which the light source of the pointer is perceived by the patient as a double image. In a preferred examination method, this procedure for different directions of eccentricity is repeated.

The present examination method can be used, as desired, together with a helmet and/or glasses, which can accommodate the optical elements, such as prisms, filters and spherical lenses or even a cross projector, a distance measuring system and/or a tracking unit.

In using a camera system for observing the patient, it can be implemented in such a manner that a frontal observation of the patient is possible in order to monitor his posture during the examination, to document photographically the position of the eyes or to measure objectively with the aid of the closed eyelid reflex images (Purkinje reflex) with suitable illumination the position of the eyes, using suitable image processing means.

The position sensor mechanisms for detecting the position of the patient's head and/or the indicator means are designed in accordance with the special features. Their function can be divided into degrees of freedom, namely three degrees of freedom for the orientation in space and three degrees of freedom for the position in space. In the case of a completely unfixed indicator or a completely unfixed head position, a position sensor mechanism is to be used that allows the measurement of five to six degrees of freedom. In contrast, a partially fixed pointer or a system with partial fixation of the head position requires a position sensor mechanism that need only measure between one to five degrees of freedom.

The examination system can include a hand or foot-operated switch or pushbutton, which is operated by the examining individual or by the patient, and can serve in particular for detection of the measurement results or for control of the takeover of the measurement values by the computer, when the patient has localized a double image.

The aforementioned fusion/side separation can be carried out not only with the aid of a dark red glass, as stated above, but also with other colored filters or combinations of colored filters, e.g., with red/green glasses. Similarly the lamps or LEDs that are used do not have to be designed exclusively for white light, but rather, for example, also as red/green light sources that can be switched over. Similarly the use of polarizing filters on the device and patient side is possible.

To measure the cyclo-rotation, a sensor, such as a potentiometer, can be used instead of or in addition to a stepping motor.

When there are several sensors for an ultrasound distance measurement, it can be used to measure not only the distance, but also the position in space. Hence, changes in the position of the head with respect to the device can be detected not only with respect to the distance, but also in the lateral direction by means of a triangulation method, wherein preferably a transmitter is positioned at the head of the test person and several spaced receivers are positioned at the display surface.

The measurement results, delivered by the existing sensors, are stored preferably in a database. If desired, the measurement data and/or the examination data, obtained by the computer from the measurement data, can also be transmitted over networks, e.g., over the Internet, and further processed and/or stored at an external site.

Measurement data can be further processed (either locally at the examination site or, as stated, at a distant evaluation site) by using, as mentioned previously, neural networks or expert systems or by implementing suitable evaluation algorithms. Thus, for example, the measurement results can be analyzed automatically by the computer to the effect that the lines of sight are found along the horizontal, vertical and radial axes. For diagnostic purposes the evaluation data can be interpreted preferably in turn automatically by the computer in order to determine possible eye dysfunctions. Furthermore, owing to the computer means the system can make automatically not only an evaluation or diagnosis, but also with a corresponding layout of the system, it can give suitable suggestions regarding therapy in the sense of precise qualitative and quantitative instructions, for example, to the extent which prism strength in which axis of vision should be chosen, which diopter number is expedient and/or which eye muscles should be changed by how many millimeters. In this respect the system performs a largely automated eye examination procedure and thus goes far beyond data detection.

The aforementioned LED and other light sources can be used, as desired, with light guides, where the actual light source is arranged at a spatial distance from the display surface; and the light can be guided over the light guide to the display surface. The corresponding light guide end is then positioned at the point at which the actual light sources are located in the described embodiment. This measure is of significant technical importance, especially when the sensor mechanism is disturbed by consumers.

In summary it must be stressed once again that the invention permits a largely automated ocular motility examination is possible, during which any deviation from the x/y coordinate closeby is realized by using a large area, sensitive display surface or faraway by using a position sensor mechanism, which detects spatially the position of the indicator means and/or the position of the patient's head according to one to six degrees of freedom. The system itself can perform both qualitative and quantitative interpretation of the measurement data regarding the ocular motility. Furthermore, by means of an expert system, suitable algorithms and/or a neural network with the aid of a computer at the examination place or an external computer that is connected, for example, to the Internet, it can perform an automatic analysis and further processing of the data with respect to evaluation, diagnosis and/or therapy.

Description of the Data Analysis and Data Processing

FIG. 5a is an exemplary representation of measurement points with radial eccentricity of 0 degrees, 20 degrees and 30 degrees. Of course, the eccentricities/lines of sight to be examined can be varied or expanded. FIG. 5b is a representation of the measured angles of squint in a double image scheme. (For a better overview of the assignment, the eccentricities, and not—as customary—the angles of squint, were entered into the scheme.) If only the measured angles of squint are to be shown, the angles of squint/cyclo-rotation for the horizontal and/or vertical deviations can be entered into this scheme. For better visualization, the angles of squint can be entered in levels of gray or color coded or shape/pattern coded by suitable highlighting. The described linearized representation of the measured eccentricities is not automatically necessary. Similarly a representation could follow in a scheme of radial structure. However, a linearized representation is advantageous, since it can be simply converted into a matrix structure, known from mathematics. Thus, well-known arithmetical operations, associated with such a matrix structure, can be performed for further processing the results.

Figure 5:
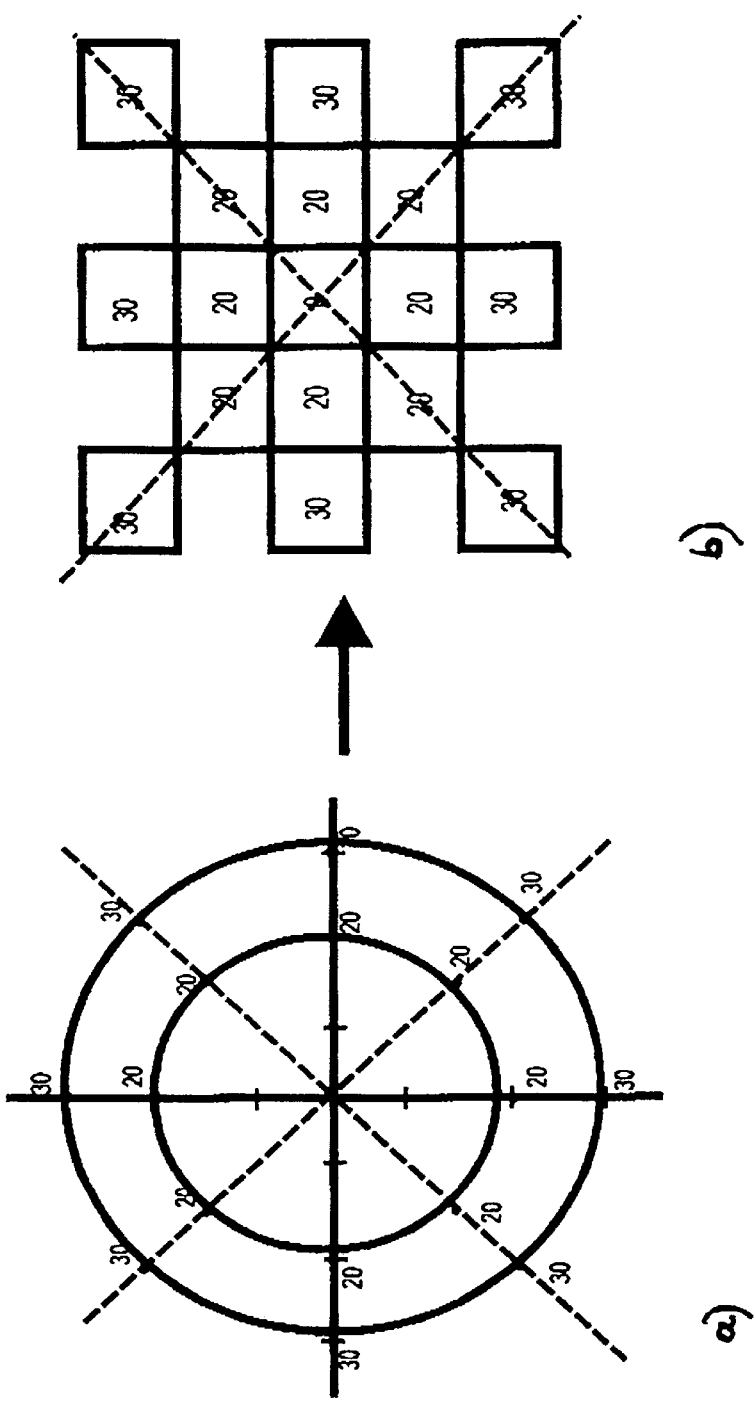
FIG. 5 is a graphic representation of the results of the raw data regarding the angle of squint.
Figure 6:
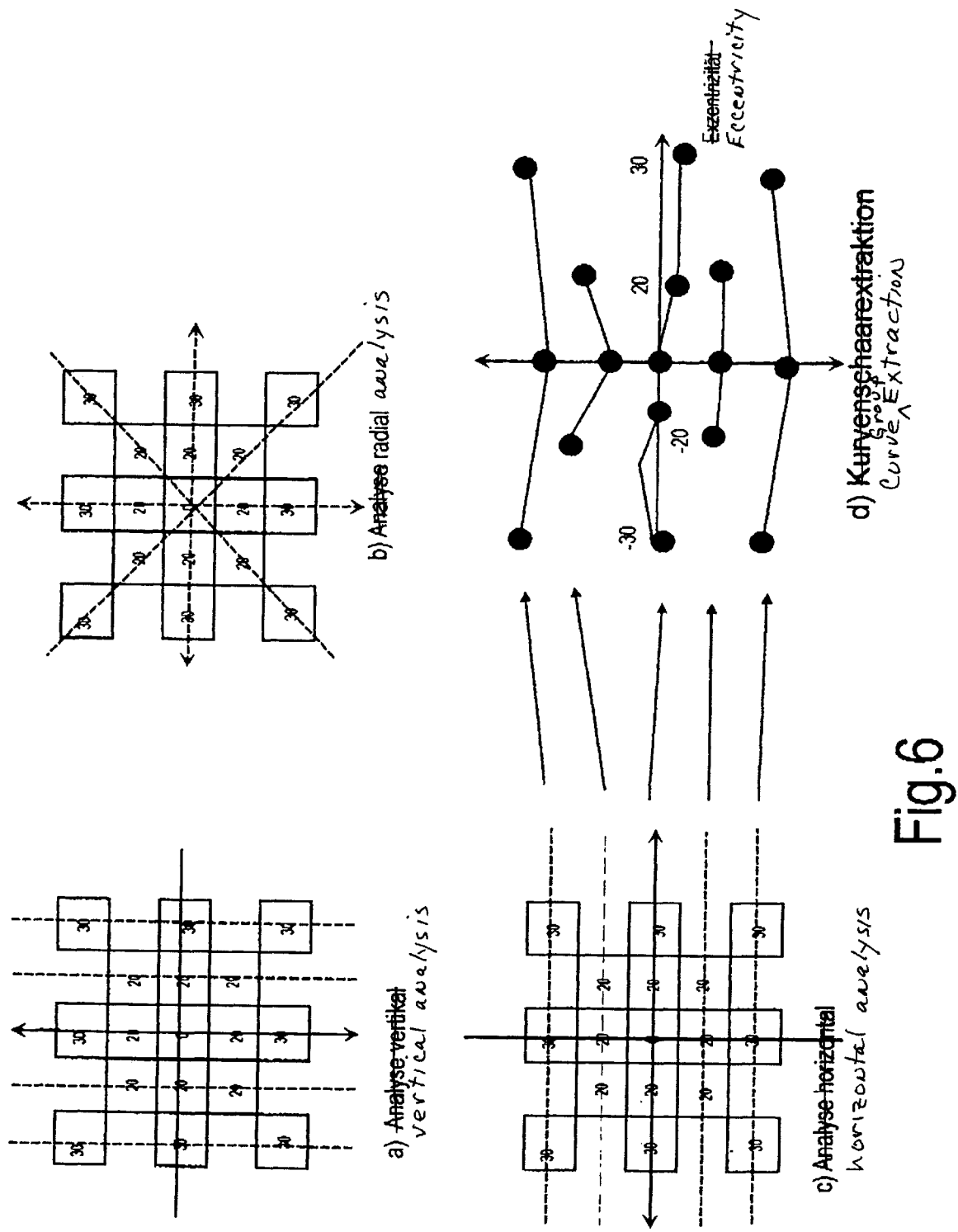
FIG. 6 is a graphic representation of a procedure for extracting the family of curves.

FIG. 6 shows the matrices from the double image scheme, explained by way of an example in FIG. 5. The analysis can be performed with operations of the matrix algebra, known from mathematics. The FIGS. 6a–c show possible operations (vertical, radial, horizontal analysis) of the systematic analysis of a double image matrix. In this respect the directions of the data analysis correspond to the possible vertical, horizontal, radial or rotational movements of the eye. FIG. 6d) depicts by way of an example the extraction of a family of curves according to the horizontal analysis possibility. In accordance with each axis shown in the matrix scheme, a curve was extracted. These curves can be analyzed just like single values.

Figure 4:
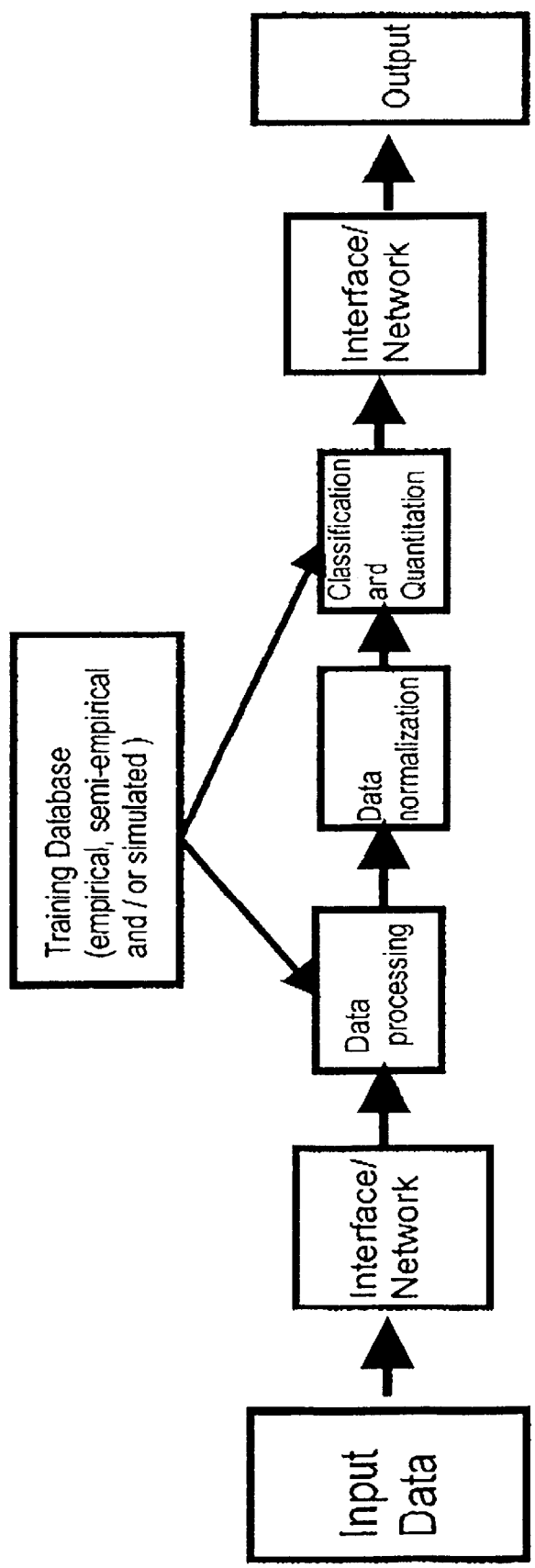
FIG. 4 is a flow chart of the data analysis according to the invention.

FIG. 4 shows the process flow of an analysis or autointerpretation unit, and in particular, different modules of a possible automated evaluating algorithm (expert system, neural network, among others evaluating algorithms), which can be used for the sake of a better overview or also as a diagnostic and/or therapeutic aid. As a function of the user's requirements, the system can be expanded or reduced by modules. Furthermore, the order of sequence or the interconnections of the modules can also be varied. Furthermore, a parallel or sequential arrangement of the modules or structures within the modules is also feasible.

The process chain starts with the raw data (input data), obtained from the examination of the patient. Depending on the system, these data are fed directly to the evaluating modules or fed first to the evaluation system over a network (interface/network), such as the Internet or another telemedical link. This also applies to the data output. The computerized data evaluation covers in total a wide spectrum, ranging from the simple preparation of data, such as color coding or intensification, to the "intelligent diagnosis".

At this point the individual modules are explained in detail below.

Input data: (data input) In addition to the measurement data that are found, other data regarding age, refraction, visual acuity, behavior during the examination (constant distance, head movements . . . ), existing diagnoses, etc. can be entered here.

Interface/Network: This module represents the interface to the autointerpretation system. In the case of data processing in the sense of telemedicine, the local data or the preprocessed data are fed over a teleconnection or a network to the autointerpretation system. Of course, databases for storing the raw data that were found can also be transmitted over teleconnections or in the sense of the training database explained below.

Data Processing: Here data are further processed: Curve group extraction with curve analysis (gradient . . . ), filter operations, linear and non-linear pattern/curve matching, principal component analysis (PCA), learning vector extraction, data reduction methods, interpolation and the like.

Data Normalization: Amplitude normalization, standardized data preparation.

Classification and Quantitation: Core of the interpretation, linear/non-linear adjustment, multilayer/monolayer perceptron neural network . . . , statistical classification, e.g. Bayesian . . . , application of Harms diagnostic scheme, evaluation of the curve analysis (e.g. +gradient—e.g. increasing paralysis in the left lateral gaze), etc.

Output: (binary) answers, like normal or pathological findings, improvement—deterioration . . . , data visualization, functional diagnosis, therapy suggestions, diagnosis.

Training database: This database can include empirical data (non-modified patient data), semi-empirical data (modified patient data) and calculated/simulated data with respect to the diagnosis and therapy. In so doing, both data from the normal findings and data from the pathological findings are integrated. Pathological findings are associated with diagnoses. The database can be continuously further developed either automatically or manually or trained by the system. Standardized or classified data serve for the training process.

The autointerpretation system can be used, as described above, for the pure preparation of data up to the diagnosis and therapy. If, for example, a trained database is applied to surgical therapy, the system can give by means of the individual examination data precise instructions for the qualitative and quantitative operation of eye muscles. The system can be used for both the diagnosis and the preparation of the results of the findings.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Device for examining ocular motility, comprising:
   a display device for displaying a fixation light on a display surface; and
   at least one of
   (i) an indicator that is adjustable at a location of the a test person, and that indicates a position of indicator points representing the test person's subjective visual impression, on the display surface; and
   (ii) a device for determining position and distance of the test person's head in relation to the display surface;
   wherein at least one of the following is true
   (i) the indicator includes a sensor mechanism for detecting and determining the position of an indicator point on the display surface; and
   (ii) the device for determining the position and distance of the test person's head comprises sensor means for adjustment or detection of an orientation and distance of the test person's head in relation to the display surface; and
   wherein data about at least one of i) the position of the indicator point on the display surface, and ii) the position of the test person's head in relation to the display surface are transmitted to a computerized evaluation unit, which evaluates this information to determine at least one ocular motility characteristic.

2. The device according to claim 1, wherein the display surface is approach sensitive and has an approach sensor mechanism that is part of the sensor mechanism for determining the position of the indicator point.

3. The device according to claim 1, wherein:
   the display surface comprises photosensitive means which form the sensor mechanism for determining the position of the indicator point; and
   the indicator comprises a light pointer, which is operatable by the test person and whose purpose is to generate a spot of light as an indicator point on the display surface.

4. The device according to claim 1, wherein:
   the indicator includes a pointer which can be operated by the test person and is spatially totally or partially unfixed; and
   the sensor mechanism for determining the position of the indicator point detects the position of the pointer according to at least one degree of freedom in three dimensional space, for the purpose of determining the position of the indicator point on the display surface.

5. The device according to claim 1, wherein:

the display surface includes photosensor means; and the device for determining the position of the test person's head comprises a headlight projection unit, which can be fixed at the test person's head and which generates a spot of light that indicates the position of the head, on the photosensitive display surface.

6. The device according to claim 1, wherein the device for determining the position of the test person's head comprises a tracking system, which is worn at the test person's head and which detects the position of the test person's head according to at least one degree of freedom in three dimensional space.

7. The device according to claim 1, wherein the device for determining the position of the test person's head comprises one of an ultrasound distance measuring device and an optical distance measuring device for detecting the distance of the test person's head from the display surface.

8. The device according to claim 1, further comprising a video camera system with image evaluator for detecting one of:

the spatial position of the test person's head;

position of a spot of light projected by a light source that is fixed at the head of the test person, on the display surface;

position of a pointer element, which touches the display surface; and position of a spot of light, projected by the pointer on the display surface.

9. The device according to claim 1, wherein:

the computerized evaluation unit contains one of a neural network, an expert system, and algorithms for diagnostic evaluation of information provided by the device for determining the position of the test person's head; and the indicator can be adjusted with respect to at least one eye motility parameter.

10. The device according to claim 9, wherein the computerized evaluation unit finds a line of sight along at least one of horizontal, vertical and radial axes.

11. The device according to claim 1, further comprising a database unit in which at least measurement data delivered by the sensor(s), can be stored.

12. A device for examining ocular motility, comprising:

a display device for displaying a fixation light on a display surface; and an indicator that is adjustable at the location of a test person, for indicating a position of indicator points representing the test person's subjective visual impression, on the display surface; wherein the indicator includes a sensor mechanism for detecting and determining the position of an indicator point on the display surface; and data about at least one of i) the position of the indicator point on the display surface, and ii) the position of the test person's head in relation to the display surface are transmitted to a computerized evaluation unit, which evaluates this information to determine at least one ocular motility characteristic.

13. The device according to claim 12, further comprising a device for determining position and distance of the test person's head relative to the display surface.

14. The device according to claim 13, wherein the device for determining position and distance comprises sensor means for adjustment or detection of an orientation and distance of the test person's head relative to the display surface.

15. A device for examining the ocular motility of a test person, comprising:

a display device for displaying a fixation light on a display surface;

an indicator that is adjustable at the location of a test person, for indicating a position of indicator points representing the test person's subjective visual impression, on the display surface; and a device for determining the position and distance of the test person's head in relation to the display surface, said device comprising sensor means for adjustment or detection of an orientation and distance of the test person's head in relation to the display surface;

wherein data about at least one of i) the position of the indicator point on the display surface, and ii) the position of the test person's head in relation to the display surface are transmitted to a computerized evaluation unit, which evaluates this information to determine at least one ocular motility characteristic.

16. The device according to claim 15, wherein the indicator includes a sensor mechanism for detecting and determining the position of an indicator point on the display surface.

17. A device for examining ocular motility of a test person, comprising:

a display device for displaying a fixation light on a display surface; and a device for determining the position and distance of the test person's head in relation to the display surface, said device comprising sensor means for adjustment or detection of an orientation and distance of the test person's head in relation to the display surface;

wherein data about at least one of i) the position of an indicator point that is manipulated by the test person on the display surface, and ii) the position of the test person's head in relation to the display surface are transmitted to a computerized evaluation unit, which evaluates this information to determine at least one ocular motility characteristic.

* * * * *